(12) United States Patent
Hughes

(10) Patent No.: US 7,647,640 B2
(45) Date of Patent: Jan. 12, 2010

(54) SYSTEM FOR BINDING SECRETS TO A COMPUTER SYSTEM HAVING TOLERANCE FOR HARDWARE CHANGES

(75) Inventor: Aidan T. Hughes, Bellevue, WA (US)

(73) Assignee: Microsoft Corporation, Redmond, WA (US)

( * ) Notice: Subject to any disclaimer, the term of this patent is extended or adjusted under 35 U.S.C. 154(b) by 288 days.

(21) Appl. No.: 11/876,640

(22) Filed: Oct. 22, 2007

(65) Prior Publication Data

US 2008/0098482 A1    Apr. 24, 2008

Related U.S. Application Data

(62) Division of application No. 10/378,224, filed on Mar. 3, 2003, now Pat. No. 7,296,294.

(51) Int. Cl.
- *G06F 21/22* (2006.01)
- *G06F 21/02* (2006.01)
- *G06F 7/04* (2006.01)

(52) U.S. Cl. .............................. 726/26; 726/32; 726/33; 705/56; 705/58

(58) Field of Classification Search .................. 726/26, 726/31–36; 705/56–59; 713/189
See application file for complete search history.

(56) References Cited

U.S. PATENT DOCUMENTS

| | | | | |
|---|---|---|---|---|
| 5,113,518 A | * | 5/1992 | Durst, Jr. et al. | 726/29 |
| 5,182,770 A | * | 1/1993 | Medveczky et al. | 705/56 |
| 5,790,783 A | * | 8/1998 | Lee et al. | 726/20 |
| 6,134,659 A | * | 10/2000 | Sprong et al. | 713/190 |
| 6,243,468 B1 | * | 6/2001 | Pearce et al. | 380/255 |
| 6,678,665 B1 | * | 1/2004 | Benson et al. | 705/51 |
| 2004/0107368 A1 | * | 6/2004 | Colvin | 713/202 |

FOREIGN PATENT DOCUMENTS

CA    2310032 A1 * 12/2001

OTHER PUBLICATIONS

"Inside Windows Product Activation" © 2001 Fully Licensed GmbH. http://licenturion.com/xp/fully-licensed-wpa.txt.*

Coutinho, S.C., The Mathematics of Ciphers, Chapter 7, Systems of Congruences, Published by A K Paters Ltd., pp. 107-119 (1999).*

Crandall et al. Prime Numbers, Chapter 8, The Ubiquity of Prime Numbers, Published by Springer-Verlag, pp. 351-404 (2001).*

Schneier, Bruce. Applied Cryptography, Second Edition, Published by John Wiley & Sons, Chapter 11, pp. 259-260 (1996).*

* cited by examiner

*Primary Examiner*—Kimyen Vu
*Assistant Examiner*—Thomas Gyorfi
(74) *Attorney, Agent, or Firm*—Merchant & Gould, P.C.

(57) ABSTRACT

Systems and methods for binding a secret to a computer system are disclosed. Systems and methods for generating a strong hardware identification (SHWID) for a given computer system are also disclosed. The strong hardware identification (SHWID) is coupled to a bound secret. The strong hardware identification (SHWID) may be used to control the use of software on the given computer system depending on the degree of hardware changes to the computer system.

7 Claims, 7 Drawing Sheets

SYSTEM FOR BINDING SECRETS TO A COMPUTER SYSTEM HAVING TOLERANCE FOR HARDWARE CHANGES

RELATED APPLICATION

The present application is a divisional application of co-pending U.S. patent application Ser. No. 10/378,224 for "SYSTEM FOR BINDING SECRETS TO A COMPUTER SYSTEM HAVING TOLERANCE FOR HARDWARE CHANGES," filed Mar. 3, 2003. This application claims the benefit and priority of its related application under 35 U.S.C. § 120.

FIELD OF THE INVENTION

The present invention relates to systems and methods for binding a secret to a given computer system. The present invention also relates to systems and methods for generating a strong hardware identification for a given computer system, wherein a component of the strong hardware identification is coupled to a bound secret. The resulting strong hardware identification may be used to control the use of software on the given computer system depending on the degree of hardware changes to the computer system.

BACKGROUND OF THE INVENTION

There has been considerable effort in recent years to prevent or minimize the unlawful use of computer software. Due to its reproducibility and ease of distribution, piracy of computer software and illegal use of computer software beyond the scope of a license agreement are common occurrences, which significantly hurt software manufacturers.

Methods have been developed in an effort to reduce the occurrences of computer software piracy and illegal use of computer software beyond the scope of a license agreement. However, such methods often cause problems for legitimate software purchasers and users in the form of consumer inconvenience. For instance, a user who has upgraded his/her computer should be able to legitimately reinstall the software product on the upgraded machine. However, presently available methods may either (i) not allow the software to be installed, or (ii) force the user (who is now disgruntled) to call the software manufacturer for assistance.

Accordingly, there remains a need for improved technology solutions to piracy and illicit use, but which also recognize and accommodate the needs and practices of a legitimate software purchaser and user.

SUMMARY OF THE INVENTION

The present invention addresses some of the difficulties and problems discussed above by the discovery of a method for binding a secret to a given computer system, and an improved hardware identification coupled to the secret. The hardware identification of the present invention provides a method of minimizing or preventing software piracy and the illegal use of computer software beyond the scope of a license agreement, while allowing for machine upgrades by legitimate software users.

The hardware identification of the present invention, referred to herein as a "strong hardware identification" (SHWID), comprises two separate components: (1) a hardware identification component, and (2) a partial secret component. By combining (1) a hardware identification component together with (2) a partial secret component, a more secure and reliable strong hardware identification (SHWID) for a given computer system is generated.

The strong hardware identification (SHWID) may be used to identify a given hardware configuration when loading a software product onto the computer. The strong hardware identification (SHWID) may be stored for future use, such as (i) when the same software product is launched on the same computer or a variation of the same computer, or (ii) when the same software product is reloaded onto a variation of the same computer or a completely different computer. For example, when the same software product is launched on the same computer or a variation of the same computer, a determination is made as to whether the secret, coupled to the original strong hardware identification (SHWID), can be produced. If the secret can be produced, the method of the present invention allows the software product to be launched. However, if the secret cannot be produced, the method of the present invention will not allow the software product to be launched due to changes to the original hardware system beyond a desired threshold.

Accordingly, the present invention is directed to a method for binding a secret to a given computer system, and a strong hardware identification (SHWID) coupled to the secret. The present invention is further directed to a method for preventing the use of software on a computer system if the secret coupled to the original strong hardware identification (SHWID) cannot be retrieved on the computer system.

These and other features and advantages of the present invention will become apparent after a review of the following detailed description of the disclosed embodiments and the appended claims.

DETAILED DESCRIPTION OF THE INVENTION

To promote an understanding of the principles of the present invention, descriptions of specific embodiments of the invention follow and specific language is used to describe the specific embodiments. It will nevertheless be understood that no limitation of the scope of the invention is intended by the use of specific language. Alterations, further modifications, and such further applications of the principles of the present invention discussed are contemplated as would normally occur to one ordinarily skilled in the art to which the invention pertains.

The present invention is directed to a method for binding a secret to a given computer system, and a strong hardware identification (SHWID) coupled to the secret. The secret typically comprises a randomly selected whole number. The secret desirably has the following characteristics:

(1) Secret, S, is computable on hardware configuration H;
(2) Secret, S, is computable on hardware configuration $H_1$, which is hardware configuration H after an amount of component change up to a desired threshold amount of component change; and
(3) Secret, S, is virtually impossible to compute on any other hardware configuration $H_2$.

The secret may be used to generate a strong hardware identification (SHWID) for a given computer system comprising a variety of hardware components. An exemplary computer system may comprise a number of hardware component classes including, but not limited to, hard disk drives, optical disk drives such as CD-ROM drives, network cards, display adapters, read only memory (ROM), random access memory (RAM), and a basic input/output system (BIOS). An exemplary computer system and exemplary operating environment for practicing the present invention is described below.

Exemplary Operating Environment

Figure 1:
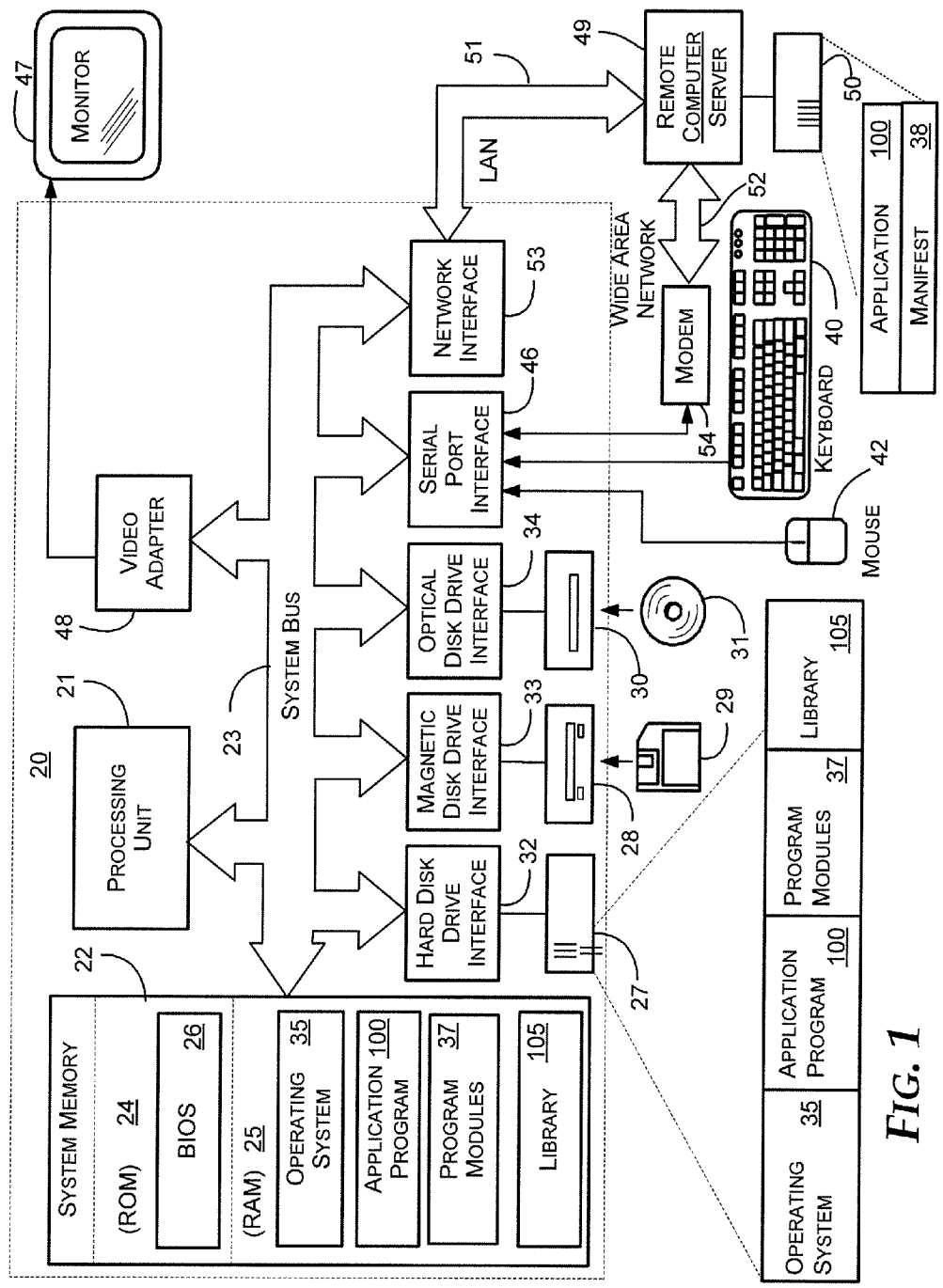
FIG. 1 is a flow diagram of some of the primary components of an exemplary operating environment for implementation of the present invention.

Exemplary embodiments of the present invention will hereinafter be described with reference to the drawings, in which like numerals represent like elements throughout the several figures. FIG. 1 illustrates an exemplary operating environment for implementation of the present invention. The exemplary operating environment includes a general-purpose computing device in the form of a conventional personal computer 20. Generally, a personal computer 20 includes a processing unit 21, a system memory 22, and a system bus 23 that couples various system components including the system memory 22 to processing unit 21. System bus 23 may be any of several types of bus structures including a memory bus or memory controller, a peripheral bus, and a local bus using any of a variety of bus architectures. The system memory includes a read only memory (ROM) 24 and random access memory (RAM) 25. A basic input/output system (BIOS) 26, containing the basic routines that help to transfer information between elements within personal computer 20, such as during start-up, is stored in ROM 24.

Personal computer 20 further includes a hard disk drive 27 for reading from and writing to a hard disk, not shown, a magnetic disk drive 28 for reading from or writing to a removable magnetic disk 29, and an optical disk drive 30 for reading from or writing to a removable optical disk 31 such as a CD-ROM or other optical media. Hard disk drive 27, magnetic disk drive 28, and optical disk drive 30 are connected to system bus 23 by a hard disk drive interface 32, a magnetic disk drive interface 33, and an optical disk drive interface 34, respectively. Although the exemplary environment described herein employs hard disk 27, removable magnetic disk 29, and removable optical disk 31, it should be appreciated by those skilled in the art that other types of computer readable media, which can store data that is accessible by a computer, such as magnetic cassettes, flash memory cards, digital video disks, Bernoulli cartridges, RAMs, ROMs, and the like, may also be used in the exemplary operating environment. The drives and their associated computer readable media provide nonvolatile storage of computer-executable instructions, data structures, program modules, and other data for personal computer 20. For example, one or more data files 60 (not shown) may be stored in the RAM 25 and/or hard drive 27 of the personal computer 20.

A number of program modules may be stored on hard disk 27, magnetic disk 29, optical disk 31, ROM 24, or RAM 25, including an operating system 35, an application program module 36, other program modules 37, and program data 38. Program modules include, but are not limited to, routines, sub-routines, programs, objects, components, data structures, etc., which perform particular tasks or implement particular abstract data types. Aspects of the present invention may be implemented as an integral part of an application program module 36 or as a part of another program module 37.

A user may enter commands and information into personal computer 20 through input devices, such as a keyboard 40 and a pointing device 42. Other input devices (not shown) may include a microphone, joystick, game pad, satellite dish, scanner, or the like. These and other input devices are often connected to processing unit 22 through a serial port interface 46 that is coupled to the system bus 23, but may be connected by other interfaces, such as a parallel port, game port, a universal serial bus (USB), or the like. A monitor 47 or other type of display device may also be connected to system bus 23 via an interface, such as a video adapter 48. In addition to the monitor, personal computers typically include other peripheral output devices (not shown), such as speakers and printers.

Personal computer 20 may operate in a networked environment using logical connections to one or more remote computers 49. Remote computer 49 may be another personal computer, a server, a client, a router, a network PC, a peer device, or other common network node. While a remote computer 49 typically includes many or all of the elements described above relative to personal computer 20, only a memory storage device 50 has been illustrated in FIG. 1. The logical connections depicted in FIG. 1 include a local area network (LAN) 51 and a wide area network (WAN) 52. Such networking environments are commonplace in offices, enterprise-wide computer networks, intranets, and the Internet.

When used in a LAN networking environment, personal computer 20 is connected to local area network 51 through a network interface or adapter 53. When used in a WAN networking environment, personal computer 20 typically includes a modem 54 or other means for establishing communications over WAN 52, such as the Internet. Modem 54, which may be internal or external, is connected to system bus 23 via serial port interface 46. In a networked environment, program modules depicted relative to personal computer 20, or portions thereof, may be stored in the remote memory storage device 50. It will be appreciated that the network connections shown are exemplary and other means of establishing a communications link between the computers may be used.

Moreover, those skilled in the art will appreciate that the present invention may be implemented in other computer system configurations, including hand-held devices, multiprocessor systems, microprocessor based or programmable consumer electronics, network person computers, minicomputers, mainframe computers, and the like. The present invention may also be practiced in distributed computing environments, where tasks are performed by remote processing devices that are linked through a communications network. In a distributed computing environment, program modules may be located in both local and remote memory storage devices.

IMPLEMENTATION OF EXEMPLARY EMBODIMENTS OF THE PRESENT INVENTION

As described above, a computer system typically comprises multiple classes of hardware components. Further, the computer system may comprise multiple components (e.g., two disk hard drives) within each class of hardware components.

The strong hardware identification (SHWID) of the present invention takes into account each component (also referred to herein as each "instance") within each class of hardware components. The strong hardware identification (SHWID) of the present invention also takes into account the secret, S, which is bound to a given computer hardware system.

An exemplary method of generating a strong hardware identification (SHWID) of the present invention is given below. Further a method of using the strong hardware identification (SHWID) as an anti-pirating tool is also described below.

I. Generating a Strong Hardware Identification (SHWID) for a Computer System

The strong hardware identification (SHWID) of a given computer system comprises two distinct components: (1) a hardware component, and (2) a partial secret component. Exemplary methods of determining each of these components are described below. The steps of the exemplary methods may be performed by software code within a software product on a customer's computer, similar to computer 20 described above with reference to FIG. 1.

A. Determining the Hardware Component of the SHWID

The SHWID of the present invention comprises a class product for each class of hardware components. The hardware component of the SHWID may be determined as shown in FIG. 2.

Figure 2:
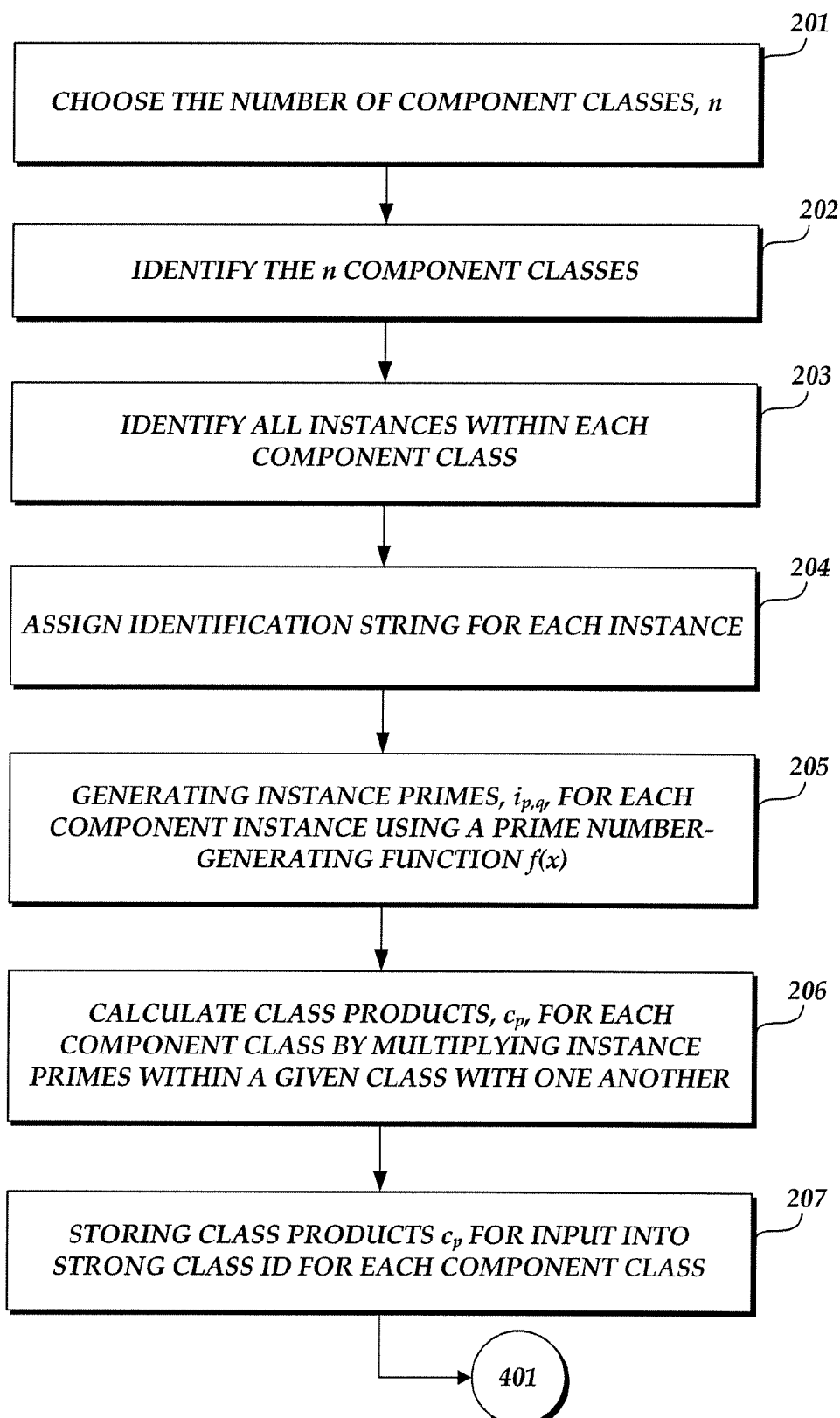
FIG. 2 is a flow diagram showing exemplary steps in determining a hardware identification component of the strong hardware identification (SHWID)

As shown in FIG. 2, an exemplary determination of the hardware component of the SHWID begins with step 201, wherein a number of component classes, n, is chosen to identify a given computer system. As discussed above, a given computer system may include a variety of hardware components and classes of hardware components. Exemplary hardware component classes include, but are not limited to, hard disk drives, optical disk drives, network cards, sound cards, display adapters, read only memory (ROM), random access memory (RAM), and a BIOS system. Desirably, n, the number of hardware component classes, is a whole number ranging from about 2 to about 16. In general, it is desirable for n to be as large as possible in order to (i) more precisely identify a given computer system, (ii) more accurately measure the degree of tolerance of a given computer system, and (iii) to enable a higher level of security for secret, S.

After choosing the number of component classes, n, in step 201, each component class is identified in step 202. The component classes may include any of the above-described component classes such as the class of hard disk drives. An exemplary list of component classes is given below in Table 1.

TABLE 1

Exemplary List of Hardware Component Classes

| Component Class No. | Class Description | Class Identifier |
|---|---|---|
| 1 | CdRom | CdRom device identifier |
| 2 | Hard Disk Drive | Drive partition serial number |
| 3 | Network Card | MAC address |
| 4 | Display adapter device | Identifier |

As shown in Table 1, in this example, n equals 4, and the identified hardware component classes are: (1) a CdRom class; (2) a hard disk drive class; (3) a network card class; and (4) a display adapter device class.

After each component class is identified in step 202, all instances within each hardware component class are identified in step 203. Desirably, each instance within a particular component class is represented by the most unique identification string associated with the instance. For example, the hardware configuration may contain a CdRom drive manufactured by NEC Corporation and having an identification string of "NEC CDRW24 S15." Any available method for determining the most unique identification string of a given instance, including device queries and operating system API function calls, may be used in the present invention. An example of a computer hardware configuration and the instances within each hardware component class is shown in Table 2 below.

TABLE 2

Exemplary Component Instances for Each Component Class

| Component Class No. | Class Description | Class Component Instances |
|---|---|---|
| 1 | CdRom | {"NEC CDRW24 S15", "TOSHIBA DVDR ASK-1425"} |
| 2 | Hard Disk Drive | {1bcdff1922, 7da90024} |
| 3 | Network Card | {00b0c31b5923} |
| 4 | Display adapter device | {"NVidia GeForce2 DDR"} |

As shown in Table 2 above, class 1, the CdRom class, contains two component instances; class 2, the disk hard drive class, contains two component instances; class 3, the network card class, contains one instance; and class 4, the display adapter device class, contains one instance.

In step 205, an instance prime is generated for each component instance using a prime number-generating function $f(x)$. Desirably, function $f(x)$ possesses the following characteristics:

(a) the result of $f(x)$ is a positive prime number;
(b) x can be any data of with length of up to about 65,000 characters; and
(c) $f(x) > 2^t$, wherein t is a whole number desirably greater than about 32. Desirably, t is equal to or greater than about 64. However, there is no limitation on the value of t.
(d) the result of $f(x)$ is deterministic based on the value of x.

Any prime number-generating function $f(x)$ may be used in the present invention to generate a prime number for each component instance. As discussed above, the prime number-generating function $f(x)$ desirably possesses the above characteristics. Suitable prime number-generating functions $f(x)$ include, but are not limited to, prime number-generating functions $f(x)$ based on the Rabin-Miller algorithm disclosed in *Applied Cryptography, Second Edition* by Bruce Schneier, pages 259-260, the disclosure of which is incorporated herein by reference in its entirety.

Table 3 below provides a list of instance primes, $i_{p,q}$, for component instances of an exemplary hardware configuration.

TABLE 3

Exemplary Instance Primes for Component Instances

| Component Class No. | Class Description | Instance Primes For Component Instances |
|---|---|---|
| 1 | CdRom | {f("NEC CDRW24 S15") = $i_{1,1}$, f("TOSHIBA DVDR ASB-1425") = $i_{1,2}$} |

TABLE 3-continued

Exemplary Instance Primes for Component Instances

| Component Class No. | Class Description | Instance Primes For Component Instances |
|---|---|---|
| 2 | Hard Disk Drive | {f(1bcdff1922) = $i_{2,1}$, f(7da90024) = $i_{2,2}$} |
| 3 | Network Card | {f(00b0c31b5923) = $i_{3,1}$} |
| 4 | Display adapter device | {f("NVidia GeForce2 DDR") = $i_{4,1}$} |

As used herein, instance prime $i_{p,q}$ is used to designate the instance prime for a given component instance, q, within a given class p. For example, instance prime $i_{1,2}$ is used to identify the instance prime for the component instance in component class 1 (e.g., p=1) and more particularly, the second component instance within component class 1 and within the computer hardware configuration (e.g., q=2).

In one embodiment of the present invention, a "salt value" may be added to the component instance identifier prior to generating the instance prime for a given component instance. In this embodiment, adding a salt value enables the production of different SHWIDs based on the same computer hardware configuration. Salt values derived from the application code or user identity enable different SHWIDs for different applications or users running on the same hardware configuration, which may be beneficial when securing data for consumption by a particular application or user only.

Once instance primes are generated for each component instance, a class product, $c_p$, is generated for each component class in step 206. Class product, $c_p$, is produced by multiplying the instance primes within a given class with one another. Exemplary class products $c_1$ to $c_4$ are given in Table 4 below.

TABLE 4

Exemplary Class Products For Each Component Class

| Component Class No. | Class Description | Class Products For Each Component Class |
|---|---|---|
| 1 | CdRom | $c_1 = (i_{1,1}) \times (i_{1,2})$ |
| 2 | Hard Disk Drive | $c_2 = (i_{2,1}) \times (i_{2,2})$ |
| 3 | Network Card | $c_3 = i_{3,1}$ |
| 4 | Display adapter device | $c_4 = i_{4,1}$ |

As shown in Table 4, the class product $c_1$ for hardware component class CdRom is equal to the product of two instances, $i_{1,1}$ and $i_{1,2}$. It should be noted that class products resulting from a single instance prime, such as class product $c_3$, may be multiplied by additional non-instance primes to increase the difficulty of factoring a given class product. This is particularly useful for class products composed of a single instance prime, such as class product $c_3$ or class product $c_4$, shown in Table 4 above. When additional non-instance primes are used to increase the class product value, it is desirable for the additional non-instance prime numbers to be in the range of greater than 2 but less than $2^t$, wherein t is an arbitrary whole number as described above. This mitigates the risk of unintended collision with instance primes from a different hardware configuration.

In step 207, each class product, $c_p$, is stored for input into the strong class identification, $C_p$, for each component class as described below. Further, as described below, the combination of each strong class identification, $C_p$, for each class is used to produce the strong hardware identification (SHWID) for a given computer hardware system. The class products $c_p$ represent the hardware component of the strong hardware identification (SHWID) for a given computer hardware system.

B. Determining the Partial Secret Component of the SHWID

Figure 3:
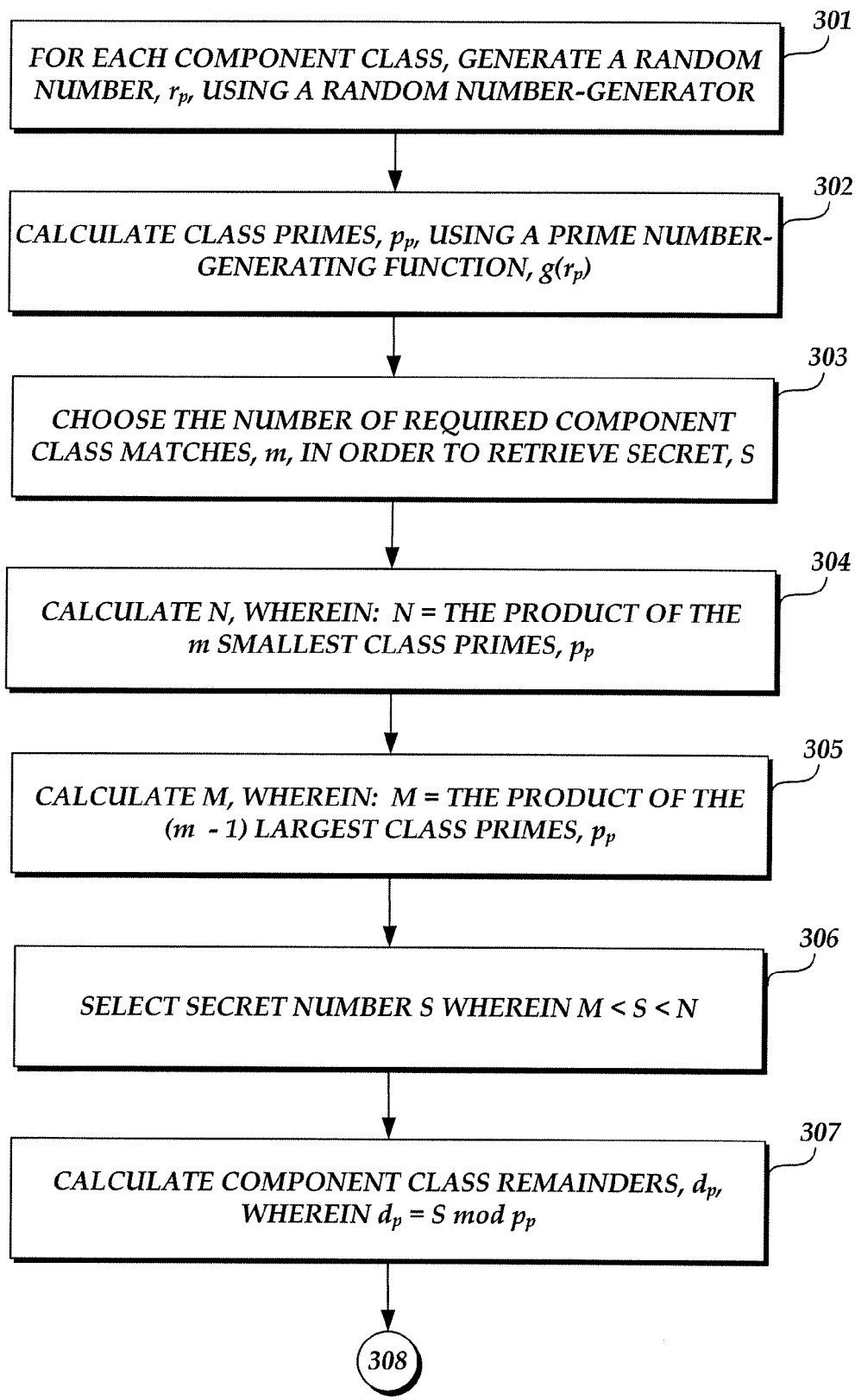
FIGS. 3-4 is a flow diagram showing exemplary steps in determining a partial secret component of the strong hardware identification (SHWID)
Figure 4:
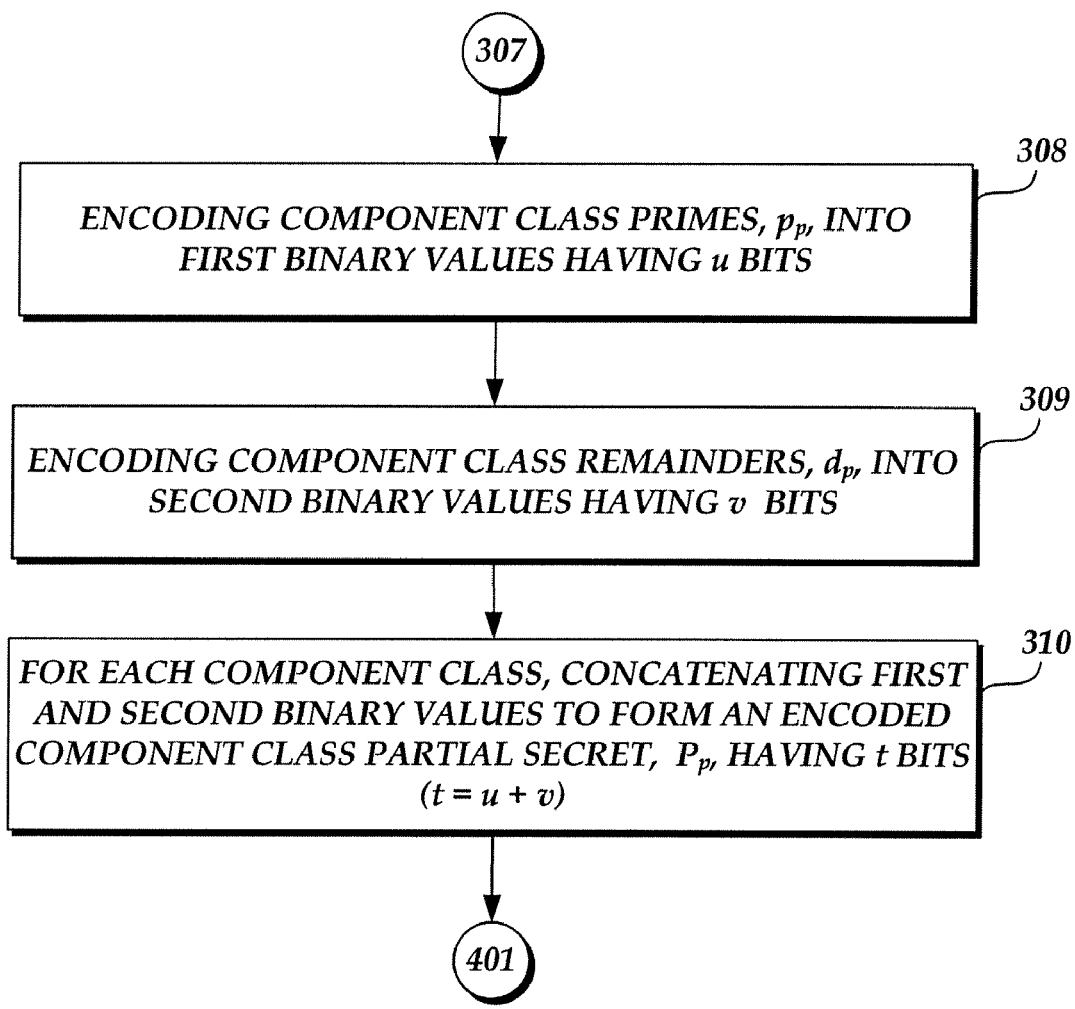

The strong hardware identification (SHWID) of the present invention also comprises a partial secret component for each class of hardware components. An exemplary method of determining the partial secret component of the SHWID is shown in FIGS. 3-4. The steps of the exemplary method may be performed by software code within a software product on a customer's computer, similar to computer 20 described above with reference to FIG. 1.

In step 301 shown in FIG. 3, a random number, $r_p$, is generated for each component class using a random number generator. Any conventional random number generator may be used to generate random number $r_p$. Suitable random number generators include, but are not limited to, random number generators disclosed in *Prime Numbers* by Crandell and Pomerance, Chapter 8, the disclosure of which is incorporated herein by reference in its entirety. Desirably, the random number $r_p$ ranges from equal to or greater than 0 up to but less than $2^u$, wherein u is less than t described above. Typically, u is approximately equal to t divided by 3.

Using the random number $r_p$ for each hardware component class generated in step 301, class primes $p_p$ are generated in step 302 using a prime number-generating function, $g(r_p)$. Desirably, the prime number-generating function $g(r_p)$ has the following characteristics:

(a) the result of $g(r_p)$ is a positive prime number;

(b) $g(r_p)$ is $<2^v$, wherein v is a whole number greater than u; and (c) u+v=t.

(d) the result of $g(r_p)$ is deterministic based on the value of $r_p$.

As with prime number-generating function $f(x)$ described above, any prime number-generating function $g(x)$ may be used in the present invention to generate a prime number for each component class random number $r_p$. As discussed above, the prime number-generating function $g(x)$ desirably possesses the above characteristics. Suitable prime number-generating functions $g(x)$ include, but are not limited to, prime number-generating functions $g(x)$ disclosed in *Applied Cryptography, Second Edition* by Bruce Schneier, pages 259-260, the disclosure of which is incorporated herein by reference in its entirety.

One example of the relationship between $g(r_p)$, t, u and v is given below.

t=64 u=20 v=44

$0 < r_p < 2^u (2^{20} = 1,048,576)$ $2 < g(r_p) < 2^v$

An exemplary list of class primes $p_p$ for each of the n classes (e.g., n=4) of an exemplary computer system is shown in Table 5 below.

TABLE 5

Exemplary Class Primes for Each Component Class

| Component Class No. | Class Description | Class Primes For Each Component Class |
|---|---|---|
| 1 | CdRom | $p_1 = g(r_1): 0 < r_1 < 2^u$ |
| 2 | Hard Disk Drive | $p_2 = g(r_2): 0 < r_2 < 2^u$ |
| 3 | Network Card | $p_3 = g(r_3): 0 < r_3 < 2^u$ |
| 4 | Display adapter device | $p_4 = g(r_4): 0 < r_4 < 2^u$ |

A sample output displaying the relationship between class primes for a given hardware configuration may be given as:

$$2 < p_2 < p_3 < p_1 < p_4 < 2^v$$

In step 303, the number of required component class matches, m, is chosen depending on the degree of tolerance desired for hardware configuration component changes. The number of required component class matches, m, may be as great as n, the total number of component classes, or may be as small as one. As m increases, the degree of tolerance to computer hardware configuration changes decreases. For example, if the total number of component classes n is equal to 4 and m is equal to 3, 3 out of 4 total component classes must match at least one component instance in order for secret S to be retrieved, which enables the loading or running of a software product. If the number of component class matches is less than 3, secret S will not be retrieved, and the software product will not run or be loaded onto the computer hardware configuration.

The number of required component class matches, m, may be predetermined by a software manufacturer and encoded into the SHWID generation method of the present invention. Once m is selected, additional parameters are determined as shown in steps 304 and 305.

In step 304, parameter N is determined, wherein N equals the product of the m smallest class primes $p_p$. For example, in the sample class prime output described above, the two smallest class primes are $p_2$ and $p_3$. If m is equal to 2, N is equal to $(p_2) \times (p_3)$.

In step 305, parameter M is determined, wherein M equals the product of the (m−1) largest class primes $p_p$. For example, in the sample class primes output given above, $p_4$ is the largest class prime. If m equals 2, then M is equal to the product of the single largest class prime, $p_4$ (i.e., (M−1)=1). It should be noted that M must be less than N to ensure that a given set of class primes has a threshold m. This is an implementation of a threshold-based secret sharing scheme as described in *The Mathematics of Ciphers* by S. C. Coutinho, Chapter 7, the disclosure of which is incorporated herein by reference in its entirety.

Once parameters N and M have been determined, secret S is selected in step 306. Secret S is greater than M but less than N. Further, secret S is any random number between M and N.

In step 307, class remainders $d_p$ are calculated using the following equation:

$$d_p = S \bmod p_p$$

An exemplary set of class remainders $d_p$ is shown below in Table 6.

TABLE 6

Exemplary Class Remainders For Each Component Class

| Component Class No. | Class Description | Class Remainders For Each Component Class |
|---|---|---|
| 1 | CdRom | $d_1 = S \bmod p_1$ |
| 2 | Hard Disk Drive | $d_2 = S \bmod p_2$ |
| 3 | Network Card | $d_3 = S \bmod p_3$ |
| 4 | Display adapter device | $d_4 = S \bmod p_4$ |

In step 308 as shown in FIG. 4, class primes $p_p$ for each component class are encoded into first binary values for each component class. Each of the first binary values has u bits. It should be noted that each class prime $p_p$ may be represented by u bits due to the following relationships:

$$p_p = g(r_p), \text{ where } 0 <= r_p < 2^u$$

$p_p$ may be represented by $r_p$ if $g(r_p)$ is available at retrieval time $r_p$ can be represented in u bits $p_p$ may be represented by $r_p$ if $g(r_p)$ is available at retrieval time if the prime number-generating function g( ) is known for the following reason. When $p_p$ is equal to $g(r_p)$ and the prime number-generating function g( ) is known, then knowing $r_p$ is sufficient to regenerate $p_p$ by executing g( ) with the parameter $r_p$. Encoding $r_p$ requires u bits (or 20 bits in the above example), while $p_p$ requires v bits (or 44 bits in the above example). A savings in the required number of bits is realized by representing $p_p$ as $r_p$.

In step 309, each of the class remainders $d_p$ are encoded into second binary values for each component class. The second binary values may be represented by v bits. It should be noted that class remainders $d_p$ may be represented by v bits as a result of the following relationships:

$$d_p = S \bmod p_p$$

$$0 < p_p < 2^v$$

Therefore, $d_p < 2^v$

In step 310, the first binary value generated in step 308 is concatenated with the second binary value from step 309 to form an encoded component class partial secret, $P_p$, having a total of t bits (i.e., t=u+v). A component class partial secret $P_p$ is generated for each component class.

It should be noted that the class partial secret $P_p$ for a given component class may contain unused bits, z, due to the second binary value having less than v bits. In this case, the unused bits, z, may be populated with random noise to prevent an attacker, who knows the qualities of $g(r_p)$, to evaluate the encoded class partial secret $P_p$ in an attempt to determine a class partial secret, $P_p$. For example, when $p_p$ is in the range $2\text{-}2^v$, $d_p$ is always $<p_p$. If $p_p$ is significantly less than $2^v$, then $d_p$ will require significantly less than v bits to encode. An attacker could make guesses about the size of $p_p$ based on the values of $d_p$. Adding random noise to fill the unused [v−(size of ($d_p$))] bits of $d_p$ helps conceal the size of $p_p$.

C. The SHWID for a Computer System

Figure 5:
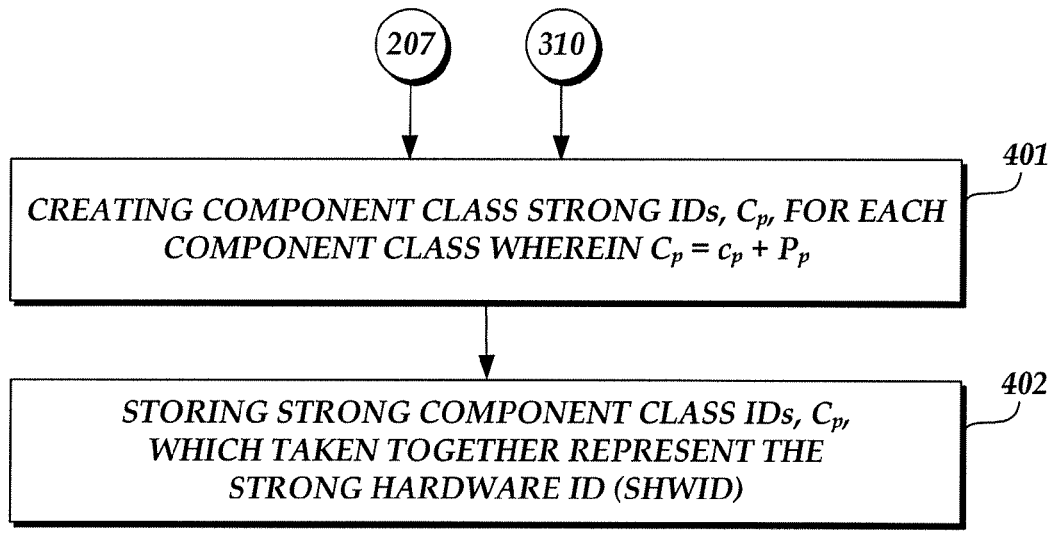
FIG. 5 is a flow diagram showing exemplary steps of combining the hardware identification component and the partial secret component of the strong hardware identification (SHWID)

The strong hardware identification (SHWID) may now be configured using the class products, $c_p$, obtained in step 207 and the class partial secret, $P_p$, obtained in step 310. As shown in step 401 in FIG. 5, class strong identifications (IDs), $C_p$, are created for each component class, wherein $C_p = c_p + P_p$. In step 402, all of the class strong IDs, $C_p$, for the component classes are combined to form the strong hardware identification (SH- WID). The resulting SHWID is stored for future retrieval. The SHWID may be stored locally (e.g., in the registry, file system, or secure store) or in an accessible remote location (e.g., a database).

It should be noted that increased security may be obtained by increasing the value of t in order to produce a class partial secret having a greater number of bits.

II. Retrieving a Secret from a Computer System Using the Strong Hardware Identification (SHWID)

The present invention is further directed to a method of retrieving or attempting to retrieve a bound secret S from a given computer hardware configuration. In one embodiment of the present invention, the method of attempting to retrieve bound secret S from a given computer hardware configuration is initiated (i) during installation of a software product, (ii) during loading of a software application already existing on a component of the hardware configuration, or (iii) both. An exemplary method for retrieving bound secret S from a hardware configuration is described in FIGS. 6-7. The steps of the exemplary method may be performed by software code within a software product on a customer's computer, similar to computer 20 described above with reference to FIG. 1.

Figure 6:
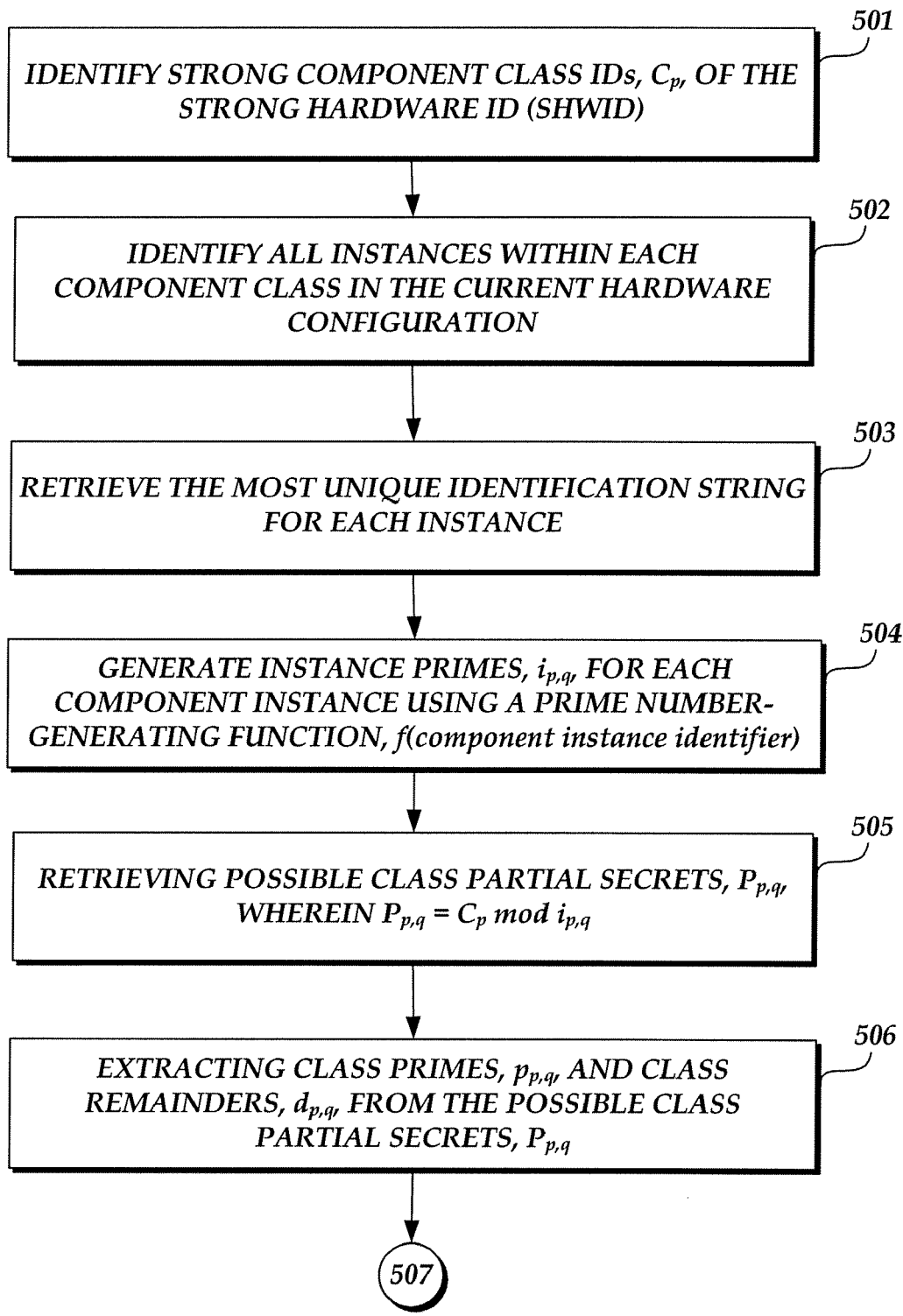
FIGS. 6-7 is a flow diagram showing exemplary steps in determining whether a software product can be used on a computer hardware system using the retrieval of a bound secret as the software product enabling factor.

In step 501 as shown in FIG. 6, the strong class IDs, $C_p$, of the strong hardware identification (SHWID) are identified for a given computer hardware configuration. For purposes of illustrating the present invention, the method of retrieving bound secret S from three separate hardware configurations, H, $H_1$ and $H_2$, will be described using a previously stored strong hardware identification (SHWID) determined from hardware configuration, H. The three distinct hardware configurations comprise (i) the exact hardware configuration H to which the SHWID was issued; (ii) a hardware configuration $H_1$, which comprises hardware configuration H having one or more component changes within an acceptable tolerance level; and (iii) hardware configuration $H_2$, which represents hardware configuration H having enough component changes such that hardware configuration $H_2$ is out of tolerance compared to hardware configuration H.

An exemplary set of strong class IDs for hardware configurations H, $H_1$, and $H_2$ is given below in Table 7.

TABLE 7

Exemplary Strong Class IDs For A Hardware Configuration

| Component Class No. | Class Description | Strong Class IDs |
|---|---|---|
| 1 | CdRom | $C_1$ |
| 2 | Hard Disk Drive | $C_2$ |
| 3 | Network Card | $C_3$ |
| 4 | Display adapter device | $C_4$ |

In step 502, all instances within each component class of a given hardware configuration are identified. As described above, any conventional method may be used to identify each component instance. Typically, a component instance is identified by the most unique identification string for the component. Exemplary identification strings for each component instance within sample configurations H, $H_1$ and $H_2$ are shown below in Tables 8-10.

TABLE 8

Exemplary Component Instances For Hardware Configuration H
Configuration H

| Component Class No. | Class Description | Component Instances |
|---|---|---|
| 1 | CdRom | {"NEC CDRW24 S15," "TOSHIBA DVDR ASB-1425"} |
| 2 | Hard Disk Drive | {1bcdff19, 7da90024} |
| 3 | Network Card | {00b0c31b5923} |
| 4 | Display adapter device | {"NVidia GeForce2 DDR"} |

TABLE 9

Exemplary Component Instances For Hardware Configurations $H_1$
Configuration $H_1$

| Component Class No. | Class Description | Component Instances |
|---|---|---|
| 1 | CdRom | {"NEC CDRW24 S15," "SONY DVD 1221"} |
| 2 | Hard Disk Drive | {8146af92} |
| 3 | Network Card | {00c0c21b5933} |
| 4 | Display adapter device | {"NVidia GeForce2 DDR"} |

TABLE 10

Exemplary Component Instances For Hardware Configuration $H_2$
Configuration $H_2$

| Component Class No. | Class Description | Component Instances |
|---|---|---|
| 1 | CdRom | {"SONY DVD 1221"} |
| 2 | Hard Disk Drive | {8146af92} |
| 3 | Network Card | {00c0c21b5933} |
| 4 | Display adapter device | {"NVidia GeForce2 DDR"} |

Once all instances within each component class of a given hardware configuration are identified, the most unique identification string for each instance is retrieved as shown in step 503. The identification strings for each instance are used to generate instance primes for each component instance using a prime number-generating function $f$(component instance identifier), as shown in step 504. Prime number-generating function, $f$(component instance identifier) may be any prime number-generating function known to those of ordinary skill in the art as described above. Tables 11-13 below provides exemplary instance primes for each of the component instances within sample hardware configurations H, $H_1$ and $H_2$.

TABLE 11

Exemplary Instance Primes, $i_{p,q}$,
For Sample Hardware Configuration H
Configuration H

| Component Class No. | Class Description | Instance Primes |
|---|---|---|
| 1 | CdRom | {f("NEC CDRW24 S15") = $i_{1,1}$, f("TOSHIBA DVDR ASB-1425") = $i_{1,2}$} |

TABLE 11-continued

Exemplary Instance Primes, $i_{p,q}$, For Sample Hardware Configuration H

| Component Class No. | Class Description | Instance Primes |
|---|---|---|
| 2 | Hard Disk Drive | {f(1bcdff19) = $i_{2,1}$, f(7da90024) = $i_{2,2}$} |
| 3 | Network Card | {f(00b0c31b5923) = $i_{3,1}$} |
| 4 | Display adapter device | {f("NVidia GeForce2 DDR") = $i_{4,1}$} |

TABLE 12

Exemplary Instance Primes, $i_{p,q}$, For Sample Hardware Configuration $H_1$

| Component Class No. | Class Description | Instance Primes |
|---|---|---|
| 1 | CdRom | {f("NEC CDRW24 S15") = $i_{1,1}$, f("SONY DVD 1221") = $i_{1,3}$} |
| 2 | Hard Disk Drive | {f(8146af92) = $i_{2,3}$} |
| 3 | Network Card | {f(00c0c21b5933) = $i_{3,1}$} |
| 4 | Display adapter device | {f("NVidia GeForce2 DDR") = $i_{4,1}$} |

TABLE 13

Exemplary Instance Primes, $i_{p,q}$, For Sample Hardware Configuration $H_2$

| Component Class No. | Class Description | Instance Primes |
|---|---|---|
| 1 | CdRom | {f("SONY DVD 1221") = $i_{1,3}$} |
| 2 | Hard Disk Drive | {f(8146af92) = $i_{2,3}$} |
| 3 | Network Card | {f(00c0c21b5933) = $i_{3,2}$} |
| 4 | Display adapter device | {f("NVidia GeForce2 DDR") = $i_{4,1}$} |

It should be noted that component instance {f("SONY DVD 1221"} is designated $i_{1,3}$ given that this type of CdRom is the third type of CdRom considered in the above hardware configurations (i.e., H, $H_1$ and $H_2$).

In step 505, all of the possible class partial secrets $P_{p,q}$ are determined, wherein $P_{p,q}$ equals $C_p$ mod $i_{p,q}$. As described above, the strong class ID, $C_p$, for each component class results from the sum of the class product $c_p$ plus the class partial secret $P_p$ for each class. If the strong class ID, $C_p$, is divided by an instance prime $i_{p,q}$ that was present in the original hardware configuration H on which the strong hardware ID (SHWID) was based, the remainder following a (mod) operation provides a possible class partial secret $P_{p,q}$. Exemplary possible class partial secrets $P_{p,q}$ for sample hardware configurations H, $H_1$ and $H_2$ are given below in Tables 14-16.

TABLE 14

Exemplary Possible Class Partial Secrets $P_{p,q}$ For Each Component Instance In Sample Hardware Configuration H

| Component Class No. | Class Description | Possible Class Partial Secrets |
|---|---|---|
| 1 | CdRom | $P_{1,1} = C_1$ mod $i_{1,1}$, $P_{1,2} = C_1$ mod $i_{1,2}$ |
| 2 | Hard Disk Drive | $P_{2,1} = C_2$ mod $i_{2,1}$, $P_{2,2} = C_2$ mod $i_{2,2}$ |
| 3 | Network Card | $P_{3,1} = C_3$ mod $i_{3,1}$ |
| 4 | Display adapter device | $P_{4,1} = C_4$ mod $i_{4,1}$ |

TABLE 15

Exemplary Possible Class Partial Secrets $P_{p,q}$ For Each Component Instance In Sample Hardware Configuration $H_1$

| Component Class No. | Class Description | Possible Class Partial Secrets |
|---|---|---|
| 1 | CdRom | $P_{1,1} = C_1$ mod $i_{1,1}$, $P_{1,3} = C_1$ mod $i_{1,3}$ |
| 2 | Hard Disk Drive | $P_{2,3} = C_2$ mod $i_{2,3}$ |
| 3 | Network Card | $P_{3,2} = C_3$ mod $i_{3,2}$ |
| 4 | Display adapter device | $P_{4,1} = C_4$ mod $i_{4,1}$ |

TABLE 16

Exemplary Possible Class Partial Secrets $P_{p,q}$ For Each Component Instance In Sample Hardware Configuration $H_2$

| Component Class No. | Class Description | Possible Class Partial Secrets |
|---|---|---|
| 1 | CdRom | $P_{1,3} = C_1$ mod $i_{1,3}$ |
| 2 | Hard Disk Drive | $P_{2,3} = C_2$ mod $i_{2,3}$ |
| 3 | Network Card | $P_{3,2} = C_3$ mod $i_{3,2}$ |
| 4 | Display adapter device | $P_{4,1} = C_4$ mod $i_{4,1}$ |

From each of the possible class partial secrets $P_{p,q}$, random numbers $r_p$ and class remainders $d_p$ may be extracted as shown in step 506. As discussed above, class primes $p_{p,q}$ may be retrievable using function $g(r_p)$, where $r_p$ is the first u bits of the possible class partial secret $P_{p,q}$. Class remainders $d_{p,q}$ may be retrieved from the last v bits of the class partial secret $P_{p,q}$. An exemplary list of all possible class primes $p_{p,q}$ and class remainders $d_{p,q}$ for sample hardware configurations H, $H_1$ and $H_2$ are given below in Tables 17-19.

TABLE 17

Exemplary Class Primes $P_{p,q}$ And Class Remainders $d_{p,q}$ For Each Possible Class Partial Secret $P_{p,q}$ Of Sample Hardware Configuration H

| Component Class No. | Class Description | Possible Class Primes $p_{p,q}$ And Class Remainders $d_{p,q}$ |
|---|---|---|
| 1 | CdRom | $P_{1,1}$ => $p_{1,1}$, $d_{1,1}$, $P_{1,2}$ => $p_{1,2}$, $d_{1,2}$ |
| 2 | Hard Disk Drive | $P_{2,1}$ => $p_{2,1}$, $d_{2,1}$, $P_{2,2}$ => $p_{2,2}$, $d_{2,2}$ |
| 3 | Network Card | $P_{3,1}$ => $p_{3,1}$, $d_{3,1}$ |
| 4 | Display adapter device | $P_{4,1}$ => $p_{4,1}$, $d_{4,1}$ |

TABLE 18

Exemplary Class Primes $P_{p,q}$ And Class Remainders $d_{p,q}$
For Each Possible Class Partial Secret $P_{p,q}$ Of Sample Hardware
Configuration $H_1$
Configuration $H_1$

| Component Class No. | Class Description | Possible Class Primes $p_{p,q}$ And Class Remainders $d_{p,q}$ |
|---|---|---|
| 1 | CdRom | $P_{1,1}$ => $p_{1,1}, d_{1,1}, P_{1,3}$ => $p_{1,3}, d_{1,3}$ |
| 2 | Hard Disk Drive | $P_{2,3}$ => $p_{2,3}, d_{2,3}$ |
| 3 | Network Card | $P_{3,2}$ => $p_{3,2}, d_{3,2}$ |
| 4 | Display adapter device | $P_{4,1}$ => $p_{4,1}, d_{4,1}$ |

TABLE 19

Exemplary Class Primes $P_{p,q}$ And Class Remainders $d_{p,q}$
For Each Possible Class Partial Secret $P_{p,q}$ Of Sample Hardware
Configuration $H_2$
Configuration $H_2$

| Component Class No. | Class Description | Possible Class Primes $p_{p,q}$ And Class Remainders $d_{p,q}$ |
|---|---|---|
| 1 | CdRom | $P_{1,3}$ => $p_{1,3}, d_{1,3}$ |
| 2 | Hard Disk Drive | $P_{2,3}$ => $p_{2,3}, d_{2,3}$ |
| 3 | Network Card | $P_{3,2}$ => $p_{3,2}, d_{3,2}$ |
| 4 | Display adapter device | $P_{4,1}$ => $p_{4,1}, d_{4,1}$ |

Once all of the possible class primes and class remainders are determined in step 506, they represent a number of sets of congruences. S is a large number, which when divided by the possible class primes $p_{p,q}$ yields class remainders $d_{p,q}$ for a given set of congruences. Because S is carefully chosen (i.e., S is between M and N) and all of the divisors are prime, the solution to the set of congruences using the possible class primes and class remainders that falls between M and N must be S. The careful selection of S in step 306 ensures that only N matching elements of the set of congruences are required to produce the correct value for S. This is a classic threshold-based secret sharing scheme as described in *The Mathematics of Ciphers* by S. C. Coutinho, Chapter 7, the disclosure of which is incorporated herein by reference in its entirety.

It is impossible to determine which, if any, possible class primes and remainders match the desired hardware configuration ahead of time, so it is necessary to generate possible secrets for each permutation of possible class primes and class remainders by solving the discrete set of congruences presented by each permutation in step 507. As shown in step 508, the resultant possible secrets can be tested using ciphertext created for verification purposes. Such a process is described below.

In the present invention, known plaintext is encoded using secret S as a key to form ciphertext. Typically, an encrypted message (i.e., ciphertext) is accompanied by a verification token that lets a decipherer know that the message has been decrypted successfully. This is usually either a hash of the plaintext of the message or some chosen plaintext. In the present invention, chosen plaintext is desirably used for simplicity. So when the SHWID is generated, chosen plaintext (e.g. "This is the chosen plaintext") is encrypted using S (i.e., as the key) to produce ciphertext. The decoder knows both the chosen plaintext and the ciphertext.

In the above situation, the validity of a candidate for S (i.e., each of the resultant possible secrets) can be verified by deciphering the ciphertext using the candidate for S (i.e., each of the resultant possible secrets) as the key. If the resultant plaintext matches the chosen plaintext, then the candidate for S (i.e., one of the resultant possible secrets) is, in fact, S. If the resultant plaintext does not match the chosen plaintext, then the candidate for S (i.e., one of the resultant possible secrets) is not S.

Figure 7:
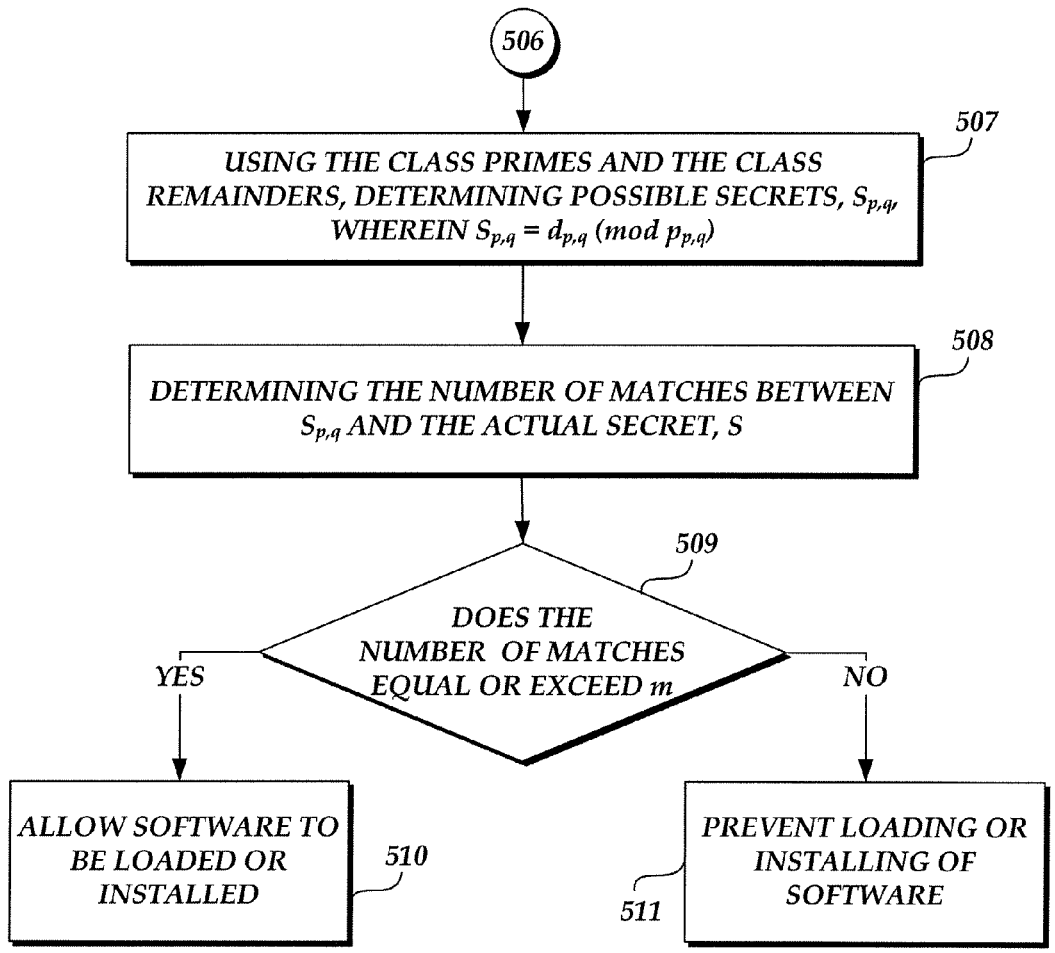

As shown in FIG. 7, if the known plaintext is revealed by decoding the ciphertext using the possible secret, then the secret S has been found and the method proceeds to step 510, wherein the program allows a given software product to be loaded or installed on the given computer hardware configuration. Otherwise, the method proceeds to step 509. If more permutations exist that have not been tested, the method returns to step 507. Otherwise, the SHWID does not match and the method proceeds to step 511, which prevents the loading or installation of the software product.

Exemplary results for sample configurations H, $H_1$ and $H_2$ are given below in Tables 20-22.

TABLE 20

Exemplary Results Showing The Number of Matches Between
Possible Secret $S_{p,q}$ and Actual Secret S For Sample
Hardware Configuration H
Configuration H

| Component Class No. | Class Description | Possible Matches Between Possible Secret $S_{p,q}$ and Actual Secret S |
|---|---|---|
| 1 | CdRom | $S = d_{1,1} \pmod{p_{1,1}}$ OR $S = d_{1,2} \pmod{p_{1,2}}$ |
| 2 | Hard Disk Drive | $S = d_{2,1} \pmod{p_{2,1}}$ OR $S = d_{2,2} \pmod{p_{2,2}}$ |
| 3 | Network Card | $S = d_{3,1} \pmod{p_{3,1}}$ |
| 4 | Display adapter device | $S = d_{4,1} \pmod{p_{4,1}}$ |

Result - Single solution, 4 of 4 match = S

TABLE 21

Exemplary Results Showing The Number of Matches
Between Possible Secret $S_{p,q}$ and Actual
Secret S For Sample Hardware Configuration $H_1$
Configuration $H_1$

| Component Class No. | Class Description | Possible Matches Between Possible Secret $S_{p,q}$ and Actual Secret S |
|---|---|---|
| 1 | CdRom | $S = d_{1,1} \pmod{p_{1,1}}$ OR $S = d_{1,3} \pmod{p_{1,3}}$ |
| 2 | Hard Disk Drive | $S = d_{2,3} \pmod{p_{2,3}}$ |
| 3 | Network Card | $S = d_{3,2} \pmod{p_{3,2}}$ |
| 4 | Display adapter device | $S = d_{4,1} \pmod{p_{4,1}}$ |

Result - Two possible solutions depending on use of $d_{1,1}$ (2 of 4 match, find S) or $d_{1,3}$ (1 of 4 match, find $Z_1$)

TABLE 22

Exemplary Results Showing The Number of Matches
Between Possible Secret $S_{p,q}$ and Actual
Secret S For Sample Hardware Configuration $H_2$
Configuration $H_2$

| Component Class No. | Class Description | Possible Matches Between Possible Secret $S_{p,q}$ and Actual Secret S |
|---|---|---|
| 1 | CdRom | $S = d_{1,3} \pmod{p_{1,3}}$ |
| 2 | Hard Disk Drive | $S = d_{2,3} \pmod{p_{2,3}}$ |

TABLE 22-continued

Exemplary Results Showing The Number of Matches
Between Possible Secret $S_{p,q}$ and Actual
Secret S For Sample Hardware Configuration $H_2$
Configuration $H_2$

| Component Class No. | Class Description | Possible Matches Between Possible Secret $S_{p,q}$ and Actual Secret S |
|---|---|---|
| 3 | Network Card | $S = d_{3,2} \pmod{p_{3,2}}$ |
| 4 | Display adapter device | $S = d_{4,1} \pmod{p_{4,1}}$ |

Result - Single solution, 1 of 4 match, find $Z_1$

As shown in Table 20 above, original hardware configuration H results in four out of four matches between possible secrets $S_{p,q}$ and actual secret S. As shown in Table 21 above, hardware configuration $H_1$ has a maximum of two matches out of four possible matches depending on which class remainder $d_{p,q}$ is used to determine possible secret S. In this sample hardware configuration, if m is equal to 2, the program allows bound secret S to be retrieved, and a software product to be loaded or installed on hardware configuration $H_1$. However, in hardware configuration $H_2$ as shown in Table 22 above, only one out of four possible matches occur. If m is equal to 2, false non-secrets $Z_1$ are produced, and the method prevents a particular software product from being loaded or installed on hardware configuration $H_2$.

The method steps described above and illustrated in FIGS. 2, 3-4, 5, and 6-7 may be performed locally or at a remote location. Typically, a customer purchases a software product that can run on a given computer, such as computer 20 shown in FIG. 1. The software product may be a shrink-wrap product having a software program stored on a transportable computer-readable medium, such as a CD-ROM or floppy diskette. Alternatively, the software product may be delivered electronically over a network, such as a local area network (LAN) 51 or a wide area network (WAN) 52. The customer loads the software product onto the computer 20 as a program stored in system memory 22.

During a software product installation, the customer is typically prompted to enter a portion of the software product identification (PID) for the software product into computer 20. The PID may be, for example, a CD key printed on a label of the shrink-wrap package. The customer enters the PID, which is associated with a software program of the software product. The PID is stored locally on computer 20 and/or remotely at an accessible location, either on a local area network (LAN) 51 or a wide area network (WAN) 52 with a third party, such as an activation authority.

As described above, during installation of the software product, a strong hardware identification (SHWID) is also generated using code within the software product or triggered by the installation of the software product. The strong hardware identification (SHWID) generated by the method of the present invention is associated with the software product identification (PID) and stored along with the software product identification (PID) locally on computer 20 and/or remotely at an accessible location, either on a local area network (LAN) 51 or a wide area network (WAN) 52, such as with a third party activation authority.

As part of the installation process, the customer may be required to activate the software product with an activation authority. This authority might be, for example, the product manufacturer or an authorized third party. The activation process is intended to force the customer to activate the software product (i) for installation and use on a specific computer or (ii) for installation and use according to terms of a product licensing agreement. Such an activation process is described in detail in U.S. Pat. No. 6,243,468, assigned to Microsoft Corporation (Redmond, Wash.), the contents of which are hereby incorporated in its entirety by reference.

The strong hardware identification (SHWID) generated by the method of the present invention and the software product identification (PID) may be stored locally on computer 20 and/or remotely at an accessible location, either on a local area network (LAN) 51 or a wide area network (WAN) 52 with an activation authority. Desirably, the software product automatically displays a graphical user interface (UI) dialog window when it is first launched, which prompt the user to initiate a connection with the activation server to activate itself. The activation server maintains a database to store received strong hardware identifications (SHWIDs) and their associated software product identifications (PIDs).

The strong hardware identification (SHWID) and associated software product identification (PID) for a given software product may be stored for an indefinite period of time until the software product is re-installed onto another computer or launched on the first computer (i.e., the computer used during the initial installation). When the same software product is re-installed onto another computer or launched on the first computer, code on the software product initiates a method of determining whether a software product can be used on a computer system according to the present invention. The software product retrieves the previously stored strong hardware identification (SHWID) associated with the software product identification (PID) of the software product either from local computer 20 or from a remote location via a local area network (LAN) 51 or a wide area network (WAN) 52. A determination is made using the previously stored strong hardware identification (SHWID) as to whether the software product can be used on a computer hardware configuration as described above.

When the use of a software product is denied due to significant changes in the hardware configuration of a first computer (i.e., the computer used during the initial installation), a dialog box may be provided to the customer indicating that the use of the software product is being denied, and that further information regarding future use of the software product may be obtained from a given source.

III. Other Uses of a Strong Hardware Identification (SHWID)

In addition to the uses described above, the strong hardware identification (SHWID) of the present invention may be used to encrypt/decrypt data for use only on a specific hardware configuration.

While the specification has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A method of determining whether a software product can be used on a second computer system having a second hardware configuration, wherein the second computer system is identical to or different from the first computer system, wherein the method comprises:

identifying the n components classes used to determine the strong hardware identification (SHWID);

identifying all instances within each component class of the second hardware configuration;

retrieving an identification string that represents each individual component instance;

generating instance primes, $i_{p,q}$, for each component instance, wherein each instance prime is a positive prime number, and wherein p represents a given component class number ranging from 1 to n, and q represents the q-th type of component within the first hardware configuration or the second hardware configuration;

retrieving possible class partial secrets, $P_{p,q}$, wherein:

$$P_{p,q} = [C_p (\bmod\ i_{p,q})];$$

extracting possible class primes, $p_{p,q}$, and possible class remainders, $d_{p,q}$, from the possible class partial secrets, $P_{p,q}$;

solving a set of congruences provided by a permutation of the possible class primes and the possible class remainders to produce a possible secret; and testing the possible secret by decoding a given ciphertext using the possible secret as the key for decoding and testing the resultant plaintext obtained by decrypting the given ciphertext with the possible secret against a corresponding known plaintext;

wherein:

if the resultant plaintext matches the known plaintext, loading the software product onto the second computer system; and if the resultant plaintext does not match the known plaintext, preventing the software product from being loaded onto the second computer system.

2. The method of claim 1, wherein the step of generating instance primes comprises inputting the identification string that represents each individual component instance into a prime number generating function, $f(x)$, wherein x is the identification string having a length of up to 65,000 characters.

3. The method of claim 2, wherein $f(x)$ generates a positive prime number having a value greater than $2^t$, wherein t is a whole number ranging from 32 to 2,048.

4. A computer readable medium having stored thereon computer-executable instructions for performing a method of determining whether a software product can be used on a second computer system having a second hardware configuration, wherein the second computer system is identical to or different from the first computer system, wherein the method comprises:

identifying the n components classes used to determine the strong hardware identification (SHWID);

identifying all instances within each component class of the second hardware configuration;

retrieving an identification string that represents each individual component instance;

generating instance primes, $i_{p,q}$, for each component instance, wherein each instance prime is a positive prime number, and wherein p represents a given component class number ranging from 1 to n, and q represents the q-th type of component within the first hardware configuration or the second hardware configuration;

retrieving possible class partial secrets, $P_{p,q}$, wherein:

$$P_{p,q} = [C_p (\bmod\ i_{p,q})];$$

extracting possible class primes, $P_{p,q}$, and possible class remainders, $d_{p,q}$, from the possible class partial secrets, $P_{p,q}$;

solving the set of congruences provided by a permutation of possible class primes and possible class remainders to produce a possible secret; and testing the possible secret by decoding a given ciphertext using the possible secret as the key for decoding and testing the resultant plaintext obtained by decrypting the given ciphertext with the possible secret against a corresponding known plaintext;

wherein:

if the resultant plaintext matches the known plaintext, loading the software product onto the second computer system; and if the resultant plaintext does not match the known plaintext, preventing the software product from being loaded onto the second computer system.

5. The computer readable medium of claim 4, wherein the step of generating instance primes comprises inputting the identification string that represents each individual component instance into a prime number generating function, $f(x)$, wherein x is the identification string having a length of up to 65,000 characters.

6. The computer readable medium of claim 5, wherein $f(x)$ generates a positive prime number having a value greater than $2^t$, wherein t is a whole number ranging from 32 to 2,048.

7. The computing system of claim 6, wherein the class product, $c_p$, for each component class is determined by the following steps:

choosing the number of component classes n;

identifying the n component classes;

identifying all instances within each component class;

assigning an identification string for each component instance;

generating instance primes, $p_{p,q}$, for each component instance, wherein each instance prime is a positive prime number, and wherein p represents a given component class number ranging from 1 to n, and q represents the q-th type of component within the first hardware configuration; and multiplying the instance primes within each component class to form class product, $c_p$, for each component class.

* * * * *